United States Patent [19]

Seligman et al.

[11] 4,375,451

[45] Mar. 1, 1983

[54] IN-SITU LEACH MEASURING SYSTEM

[75] Inventors: Peter F. Seligman, San Diego; John W. Neumeister, El Cajon, both of Calif.

[73] Assignee: The United States of America as represented by the Secretary of the Navy, Washington, D.C.

[21] Appl. No.: 257,302

[22] Filed: Aug. 13, 1981

[51] Int. Cl.³ .................. G01N 23/06; B63B 9/00
[52] U.S. Cl. .................. 422/281; 114/221 R; 114/222; 134/172; 422/53; 436/6; 436/80
[58] Field of Search .......... 422/281, 53; 23/230 C; 215/309; 114/221 A, 222, 224; 118/305; 134/167–169, 172; 436/6, 80

[56] References Cited

U.S. PATENT DOCUMENTS 3,609,916 10/1971 Hammelmann .................. 118/305
3,770,204 11/1973 Schuster ........................ 239/288.5
4,270,484 6/1981 Shimatanie et al. ............... 118/305

Primary Examiner—Michael S. Marcus
Attorney, Agent, or Firm—Robert F. Beers; Ervin F. Johnston; Thomas Glenn Keough

[57] ABSTRACT

A device and method for measuring the antifouling coating leach rates on ships' hulls uses a spherical segment shaped shell that circulates water over a coated area. A pump connected in closed circuit with the shell assures proper flow rate. A second pump creates a partial vacuum and holds the shell on the coated surface. A combination of nozzles and outlet fittings assures that the coating is exposed to a circulating flow of water. A portion of the circulated water is passed through a cupric ion electrode sensor which provides signals representative of the dissolved copper in water over time and, hence, the leach rate of the coating.

4 Claims, 9 Drawing Figures

IN-SITU LEACH RATE MEASURING SYSTEM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Currently there is a strong need for improved drag reduction and consequent fuel conservation on all ocean going vessels. Numerous antifouling coatings have been developed and several in-water hull cleaning techniques are in use or are being developed. Most of the antifouling coatings depend on a leaching action to prevent attachment of marine fouling organisms on the hull. After a time, however, the marine organisms will grow to cover portions of the wetted hull and a hull scrubbing will be needed to remove them.

Just how effectively the rejuvenated or cleaned coating resists further organisms is not clear. An ineffective coating or an untreated hull quickly becomes fouled and consequently drag and fuel consumption are increased. However, a scrubbed hull that still has enough coating to resist marine organisms is capable of providing additional months of fuel efficient, low-drag operation. Since the dry dock time, costs for recoating a hull, and in-water hull cleaning schedules are important considerations for ocean-going vessels, it is necessary to determine the maximum time a hull coating effectively resists marine organisms under various operational and cleaning conditions.

Existing laboratory techniques for the leach rate measurement call for placing an antifouling coated panel in a beaker of seawater of known volume and stirring or agitating it. At selected times small samples are removed from the solution and analyzed for copper content, by using, for example, an atomic absorption spectrophotometer. The results are used to determine the leach rate of the antifouling coating for the purposes of assessing its effectiveness and functional life. Obviously such a technique is inadequate and is not adapted for use on in-water ship hulls that pass through waters having different salinities, temperatures, etc., and have varying operational histories all of which effect leaching rate and the accumulation of marine organisms differently. In short, the laboratory methods produce results that cannot be extropolated to in-situ hull measurements or conditions.

Thus, there is a continuing need in the state-of-the-art for a method and apparatus for determining the in-situ leach rate of hull coatings which can assist in the optimization of antifouling coating design and hull cleaning procedures and in turn can lead to significant drag reduction and increased fuel conservation.

SUMMARY OF THE INVENTION

The present invention is directed to providing an apparatus and method for determining the leaching rate of a coating on a surface, specifically an underwater ship hull. The apparatus includes a means for circulating a leaching liquid on a portion of the coated surface and a means coupled to the circulating means for drawing off some of the circulated leaching liquid. A means is coupled to the drawing-off means for sensing the cupric ion concentration in the circulating leaching liquid. The circulating means includes a spherical segment shaped shell held on the hull of a ship by suction and an interconnected pump which circulates seawater over a circumscribed portion of the hull's surface. The spherical segment shaped shell has a ring-shaped lip on which is mounted a double-edged ring-shaped rubber gasket which pliably accommodates a portion of the coated hull. A plurality of nozzles and a plurality of outlet fittings are appropriately located to assure that the coated surface is washed with the water so that leached cupric ions can be detected and the leaching rate determined.

The method of determining the leaching rate of a coating on a surface calls for the circulating and recirculating of a leaching liquid on a portion of a coated surface and the drawing off of a portion of the circulated leaching fluid for sensing the cupric ion or other toxicant concentration.

A prime object of the invention is to provide a method and apparatus that allows a determination of the leaching rate of the toxicant in a hull antifouling coating.

Yet another object is to provide an apparatus and method enabling an in-situ leach rate determination.

Another object is to provide an apparatus and method of determining the hull-coating antifouling leach-rate that is portable, yet accurate.

Further object is to provide an apparatus for leaching a coated surface in the form of a spherical segment shaped shell easily emplaced by a diver.

Yet another object is to provide an apparatus for leaching a coated surface that is held in place by vacuum and maintained by a pumping action which circulates a leaching fluid (generally seawater) for ion determination.

Yet another object of the invention is to provide an apparatus for leaching a coated surface having a pliably accommodating member for engaging and isolating a washed, coated surface.

Yet another object is to provide a method and apparatus for determining leaching rates which samples recirculated fluid to enable a toxicant determination.

Other objects, advantages and novel features of the invention will become apparent from the following detailed description of the invention when considered in conjunction with the accompanying drawings.

DESCRIPTION OF THE PREFERRED EMBODIMENT

Figure 1:
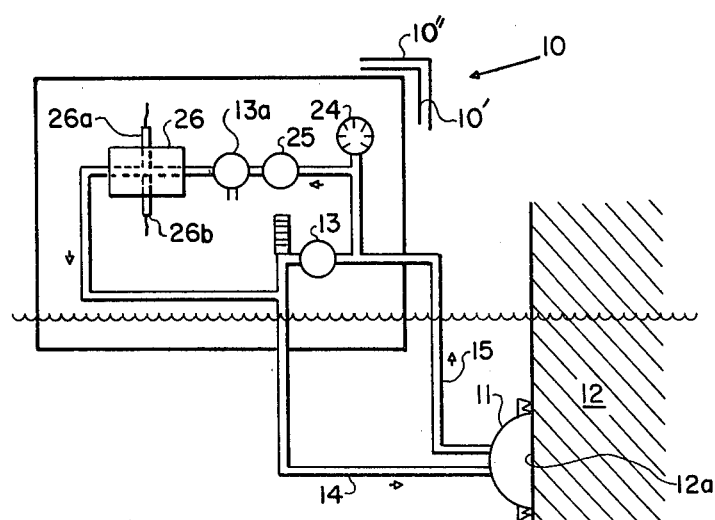
FIG. 1 is a schematical representation of the apparatus for the method of the invention.
Figure 3:
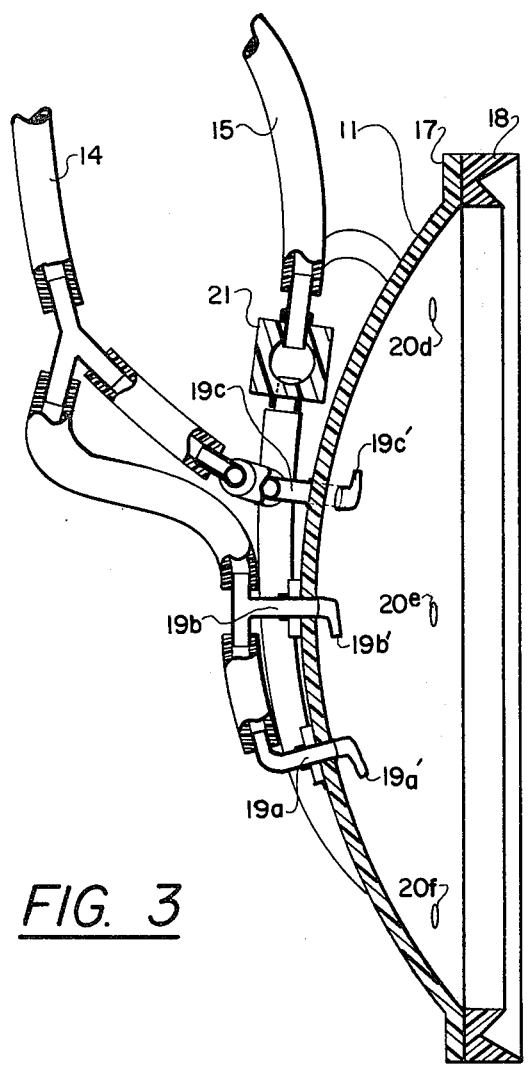
FIG. 3 is a cross-sectional representation of details of the spherical segment shaped shell taken generally along lines 3—3 in FIG. 2.

Referring now to the drawings, an in-situ leach rate measuring system 10 has its leaching device 11 mounted on a section 12a of a ship's hull 12. The entire system is compact enough to be transported on a small vessel and comes alongside ships in the harbor or the open ocean to determine the leaching rate of the ship's antifouling coatings.

The system including leaching devices to be described in detail can be duplicated, 10, 10', 10" to allow a simultaneous leach rate determination from several locations on a hull or to verify a leaching rate determination by redundancy. It would be a simple matter to combine several of the functions of the systems to be duplicated, however, for the purposes of understanding this disclosure, the entire system is duplicated when more than one leach rate indication is to be simultaneously obtained. Each system includes a pump 13 that imparts a flow of water across the antifouling coating surface sufficient to leach particles from the portion of the antifouling coating covered by its leaching device and to hold it on the ship's hull. A pair of flexible conduits 14 and 15 connect the leaching device to the rest of the system and transfer and retrieve a suitable leaching fluid such as seawater.

Figure 2:
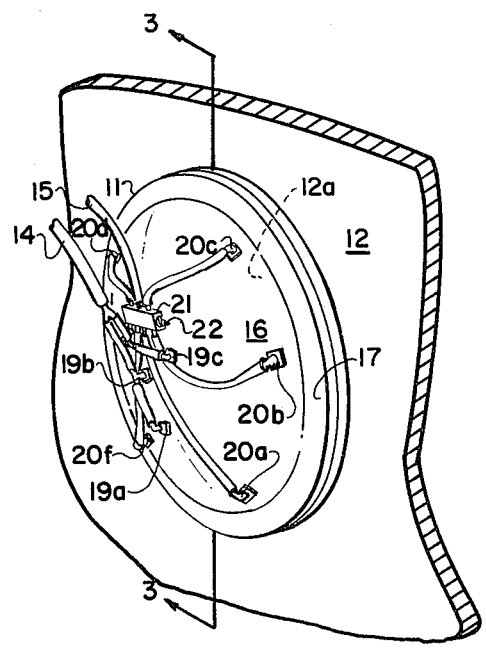
FIG. 2 is an isometric depiction of the spherical segment shaped shell operationally emplaced on a hull.

Looking to FIG. 2 of the drawings, a leaching device is shown in place on a hull. It is small enough, the outer diameter approximately thirteen inches and about four inches deep, to allow its being placed and removed by a single diver. The compact design also accommodates a variety of hull contours.

An acrylic dome 16 is provided with a ring-shaped lip 17 mounting a ring-shaped double knife edge gasket 18 bonded in place. The gasket is of the type developed by the David Taylor Naval Ship Research and Development Center, Annapolis, Md., Rubber Shop. A double edged gasket has been found more acceptable than, say, a single flat compliant strip, since this design pliably accommodates small surface irregularities on a ship's hull to assure that the leaching device maintains vacuum and remains on the hull. Fluid coming from the pump via conduit 14 enters through several inlet fittings 19a, b, c and d that have nozzles 19a', 19b' and 19c' (19d and 19d' not shown in the drawings) which direct and circulate the flow of pumped water toward the surface 12a covered by the leaching device.

Circumferentially disposed, equidistantly spaced outlet fittings 20a, b, c, d, e, and f are coupled via tubing sections to a return manifold 21 that is joined to conduit 15. The fittings 19a, b, c and d having 90° ells arranged to direct the flow in a clockwise pattern and restricted flow outlets at fittings 20a, b, c, d, e and f were found to achieve the best mixing pattern.

The rate at which the leaching liquid is pumped from manifold 21 coupled with the flow rate through the acrylic dome and directed jetting action of the flow through the nozzles assures the relatively uniform leaching and washing of exposed antifouling coating area 12s. A typical pump which has performed satisfactorily was one commercially available (e.g. Cole Parmer C-7549-19 and 7019 head) that provided a flow rate of about two liters per minute.

Having the water pumped from the acrylic dome via pump 25 assures a vacuum is maintained and that the leaching device is held in place on the ship's hull. When a test or rate determination has been finished, a diver need only open valve 22 so that the "vacuum" is released from the dome to easily remove and relocate the leaching device.

By removing liquid from the closed system via a three-way valve 13a an internal "partial vacuum" was created. In the designed system removal of approximately 300 milliliters of liquid creates a five-inch mercury vacuum and secures the leaching device to the hull. However, opening valve 22 releases the vacuum and the leaching device can be removed.

As mentioned before, three domes may be utilized simultaneously to provide statistically meaningful replications of data and to permit the simultaneous leach rate determinations on differently configured hull areas. The system shown in FIG. 1 is triplicated to provide the desired results. Each of the systems includes a vacuum gauge 24, a small peristaltic pump 25, for example, a Cole-Parmer model 7553-00, with 7015 head, and an electrode manifold 26 including an Orion cupric ion specific electrode model 94-29A and Orion referencing electrode model 90-02-00 No. 26. A flow meter 27 assures that the proper and consistent flow rate of the leaching liquid across the antifouling coating.

The electrode manifold is an appropriately machined block of plastic provided with the active cupric ion electrode and the reference electrode arranged to intercept part of the flow of seawater, for example, coming through a traverse bore. Typically, the separation between the reference electrode tips and the cupric ion specific electrode is 3 millimeters. The leaching liquid flows across and between the electrode tips so that representative signals can be picked up from the electrode to determine the copper concentration. Calibration can be performed, as in FIGS. 5 and 6, by taking sub-samples and measuring copper content by atomic absorption spectroscopy. The ion specific electrode technique is well-known and is thoroughly described by Albert Zirino et al in a 1977 article entitled "measurement of Cu concentration and Cu activity in the surface waters of the Eastern Pacific Ocean" in the *Abstracts of American Geophysical Union, Fall Meeting*, 1977, Zirino et al's article entitled "Real time analysis in Chemical oceanography" Nav. Res. ev. June, 1978 and an article by Albert Zirino and Peter Seligman entitled "Polarographic behavior of the Cu (II) ion selective electrode in seawater" appearing in a 1981 edition of Marine Chemistry.

The method of determining the leaching rate of the leaching liquid uses the cupric ion-specific electrode 26a with a double or single junction silver/silver chloride reference electrode 26b. Electrodes are commercially available which can be included in the electrode manifold, for example, both electrodes can be purchased from the Orion Research Corp. of Cambridge, Mass. The liquid junctions in the reference electrodes are filled with seawater. Potential differences are measured on a digital electrometer, a Corning Model 101 from Corning Scientific Instruments of Medfield, Mass. or a Model 101 Orion ion analyzer from Orion Research Corp. could be used to determine the potential differences between them. The calibration data generated in the course of the leach rate studies included readings indicative of the cupric ion-specific electrode potential at the times each sample circulated through the electrode manifold and a later discrete analysis of copper concentration by atomic absorption spectroscopy.

Figure 4:
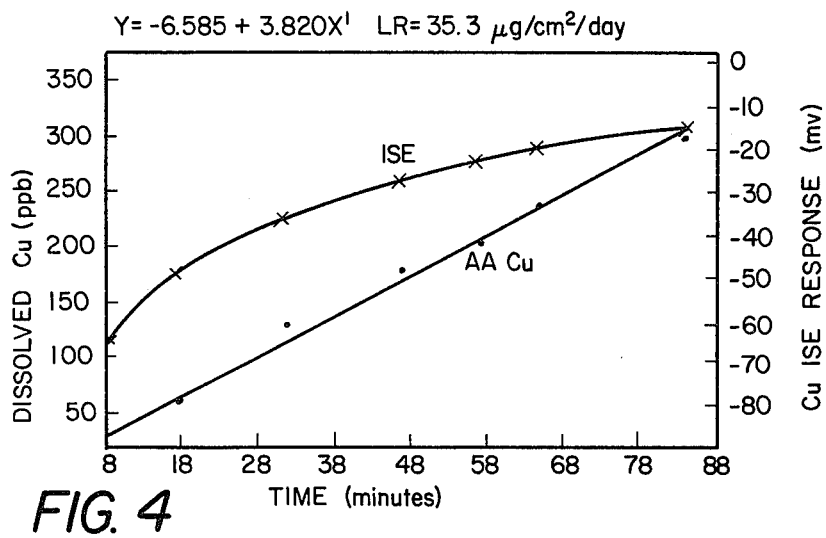
FIG. 4 shows a typical response of the cupric ion specific electrode (CSE) during in-situ leach rate measurement and total copper (Cu) concentration from atomic absorption spectroscopy.

FIG. 4 shows the response of a cupric electrode fabricated and employed in accordance with the techniques of this inventive concept. The ion sensitive electrode (ISE) response is shown to change over different periods of time.

Figure 5:
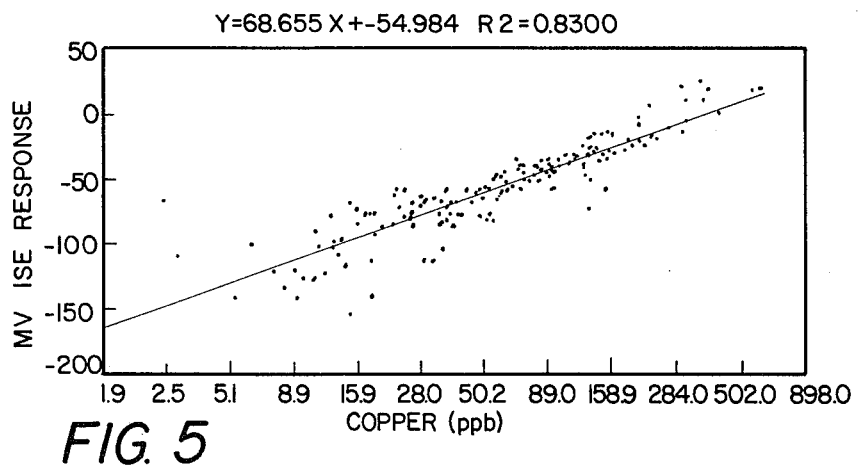
FIG. 5 is a comparison of copper ion specific electrode response during in-situ leach rate measurements to total copper concentration measured by atomic absorption spectroscopy.
Figure 6:
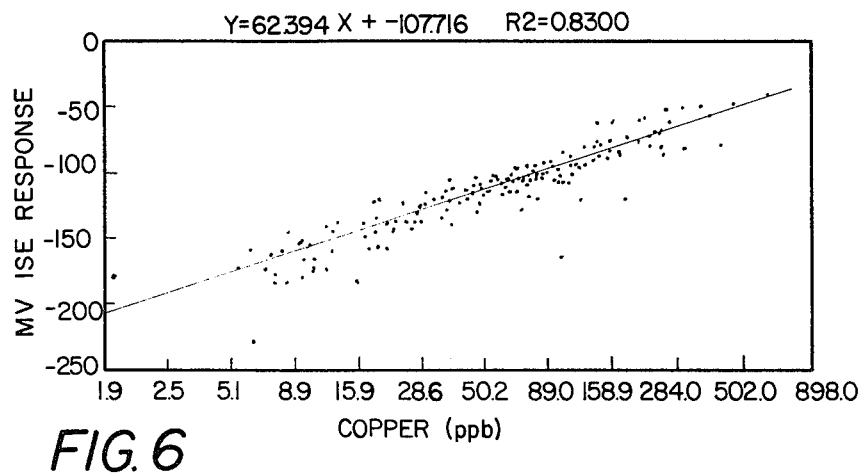
FIG. 6 is a comparison of silver-ion specific electrode response during in-situ leach rate measurements to total copper concentration measured by atomic absorption spectroscopy.

Results of the calibration studies of the cupric ion-specific electrodes are shown in FIGS. 5 and 6. These represent compilations of typical leach rate data. For comparison purposes the data presented in FIG. 6 shows the response of a silver ion-specific electrode used in hull leach studies.

The electrode response when the leaching liquid is seawater is shown to have a linear relationship with the logarithm of copper concentration. The data seems to show that the cupric ion-specific electrode response can be calibrated in seawater and is not compromised because of the chloride interference. It should be noted, however, that the electrode response slopes were decidedly nonNernstian; this high slope was due to possible interfering organic chelators and other liquids and may be due to difficulty in maintaining a reproduceable baseline potential when using cupric ion-specific electrodes for in-situ copper leach rates application. The data for the silver ion-specific electrode is more encouraging and is consistent with predicted Nernstian slope responses. Use of the silver ion-specific electrode appears to warrant further application.

Figure 7:
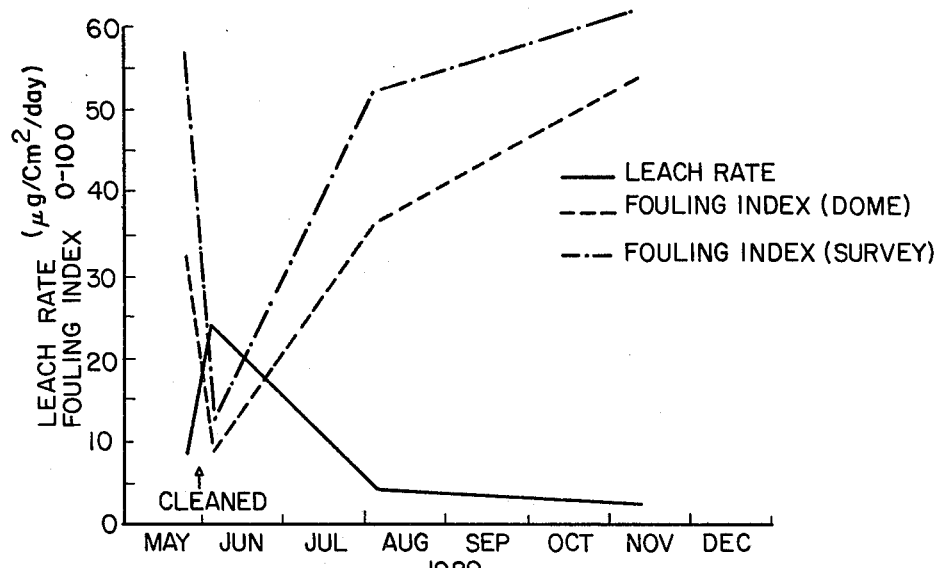
FIG. 7 shows copper leach rate and fouling index (a relative 0-100 scale) before and after in-water hull cleaning taken from averages from six locations on a ship's hull.
Figure 8:
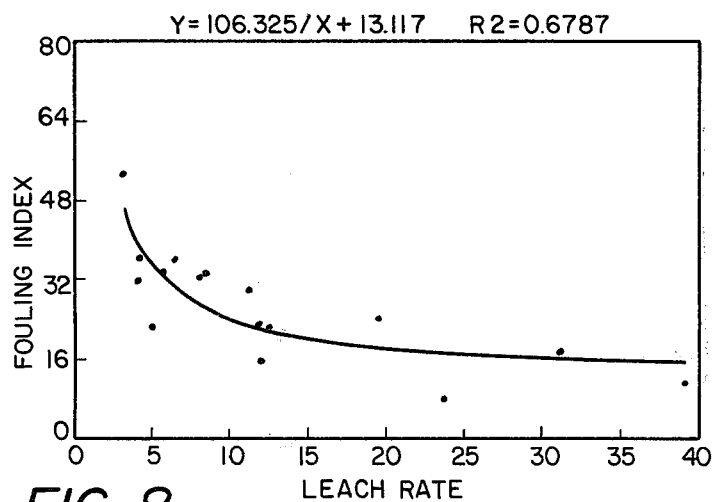
FIG. 8 shows the relationship between fouling index and in-situ leach rate from the mean values of a number of vessels.

In FIG. 7 the effects of time vs a visually established leach rate are depicted. The nearly seven-month monitoring of one hull in particular showed the changing leach rate and fouling index. The findings of FIG. 8 verified that the fouling index and leach rate can be expressed as being dependent on one another.

Figure 9:
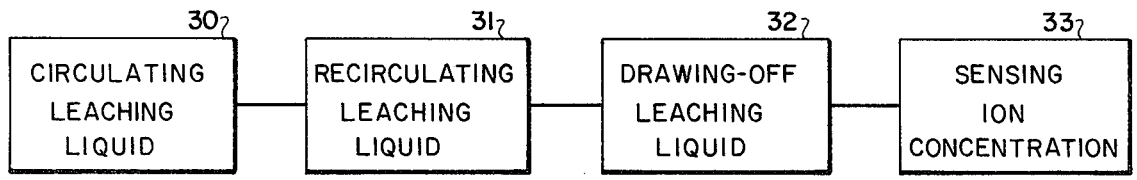
FIG. 9 is an abbreviated showing of the salient features of the method of the invention.

Referring to FIG. 1 and to FIG. 9, the function of the large peristaltic pump 13 is to pump a volume of a leaching liquid, such as seawater, through the leaching device so as to effect a circulation 30. The closed legs and pump assure a recirculating 31 of the leaching liquid. Additionally the system provides a means for sampling, or drawing-off 32 to the solution in the system. The rate of flow is regulated by appropriate adjustments to the peristaltic pump when monitored by the flow rate through flow meter 27. All three subsystems, 10, 10' and 10" may be maintained at the same rate of flow when used together or different flow rates may be tried for comparison purposes. A flow rate of 2.0 liters per minute was maintained exchanging the volume of each dome approximately every 60 seconds. The small peristaltic pump draws a small sample of the recirculating, leaching fluid from the system and directs it through the electrode manifold. Since the electrode manifold holds either a cupric or a silver ion-specific electrode and a reference electrode, to allow a sensing 33 of the ion concentration so that signals can be sent to a pH meter and then to a strip chart recorder. Sampling valve located 13a also enables an operator to collect discrete samples for other chemical analysis, however care must be taken that when these samples are taken that the vacuum in the system is not disrupted so that the leaching devices may become dislodged.

Obviously many modifications and variations of the present invention are possible in the light of the above teachings. It is therefore to be understood that within the scope of the appended claims the invention may be practiced otherwise than as specifically described.

What is claimed is:

1. An apparatus for leaching a coated surface comprising:
    a spherical segment shaped shell having a ring-shaped lip for defining an open mouth cavity;
    a double-edged ring-shaped gasket bonded onto the ring-shaped lip and disposed about the mouth of the cavity for pliably accommodating the coated surface to hold the lip on the surface and to keep ambient water out;
    means mounted on the spherical segment shaped shell for directing the flow of water therein, the directing means is a plurality of nozzles located at and near the apex of the spherical segment shaped shell and oriented to direct the flow of water onto and along the coated surface for assuring the leaching thereof;
    drawing means having a plurality of outlet fittings equidistantly circumferentially disposed near the ring-shaped lip for drawing the flow of water from along the coated surface to assure the leaching thereof; and
    means connected to the drawing means for pumping water from the spherical segment shaped shell.

2. An apparatus according to claim 1 further including:
    a manifold coupled to the pumping means and the outlet fittings.

3. An apparatus according to claim 2 in which the pumping means is a pump driven at a sufficient rate to assure a leaching of the coated surface and by removal of liquids to hold the spherical segment shaped shell on the coated surface.

4. An apparatus according to claim 3 in which the nozzles are 90° ells arranged to direct the flow in a clockwise pattern to assure the leaching of the coated surface.

* * * * *